(12) United States Patent
Duan et al.

(10) Patent No.: US 11,547,283 B2
(45) Date of Patent: Jan. 10, 2023

(54) ENDOSCOPE DEVICE AND ENDOSCOPIC DETECTION METHOD

(71) Applicant: Ankon Medical Technologies (Shanghai) Co., LTD., Shanghai (CN)

(72) Inventors: Xiaodong Duan, Pleasanton, CA (US); Shaobang Zhang, Shanghai (CN)

(73) Assignee: ANKON MEDICAL TECHNOLOGIES (SHANGHAI) CO., LTD., Shanghai (CN)

( * ) Notice: Subject to any disclaimer, the term of this patent is extended or adjusted under 35 U.S.C. 154(b) by 689 days.

(21) Appl. No.: 16/531,043

(22) Filed: Aug. 3, 2019

(65) Prior Publication Data
US 2020/0037862 A1 Feb. 6, 2020

(30) Foreign Application Priority Data
Aug. 3, 2018 (CN) .......................... 201810879377.7

(51) Int. Cl.
*A61B 1/00* (2006.01)
*A61B 1/04* (2006.01)
*A61B 1/273* (2006.01)

(52) U.S. Cl.
CPC ........ *A61B 1/00147* (2013.01); *A61B 1/0014* (2013.01); *A61B 1/00071* (2013.01); *A61B 1/00119* (2013.01); *A61B 1/041* (2013.01); *A61B 1/2733* (2013.01)

(58) Field of Classification Search
CPC . A61B 1/041; A61B 1/00089; A61B 1/00101; A61B 1/00137; A61B 1/0014; A61B 1/00154; A61B 1/00156; A61B 1/00158; A61B 1/273; A61B 1/2733; A61B 1/2736; A61B 1/31; A61B 5/07; A61B 5/6861; A61B 2562/162
See application file for complete search history.

(56) References Cited

U.S. PATENT DOCUMENTS

| | | | |
|---|---|---|---|
| 2003/0013938 A1* | 1/2003 | Iddan | A61B 1/00147 600/129 |
| 2005/0267361 A1* | 12/2005 | Younker | A61B 1/00147 600/434 |
| 2007/0299309 A1* | 12/2007 | Seibel | A61B 1/041 600/117 |
| 2012/0101331 A1* | 4/2012 | Gilad | A61B 1/041 600/114 |
| 2015/0289752 A1* | 10/2015 | Rachlin | A61B 1/00114 600/572 |
| 2018/0317755 A1* | 11/2018 | Aoki | A61B 1/00135 |

(Continued)

Primary Examiner — Ryan N Henderson
(74) Attorney, Agent, or Firm — Treasure IP Group, LLC

(57) ABSTRACT

The present invention discloses an endoscope apparatus and an endoscopic method. The endoscope apparatus includes a release source, a tether connected to the release source, an elastic clamp member and a capsule endoscope. The elastic clamp member includes an elastic clamp cavity being interconnected to an air outlet of the release source through the tether. In a clamped state, at least a portion of the capsule endoscope is within the elastic clamp cavity, wherein the elastic clamp member has a tendency to recover from deformation to apply a clamping force to the capsule endoscope. In a released state, the elastic clamp member is expanded by the air pressure from the tether, and the capsule endoscope is released from the elastic clamp cavity.

14 Claims, 12 Drawing Sheets

(56) References Cited

U.S. PATENT DOCUMENTS

2020/0037862 A1* 2/2020 Duan .................... A61B 1/0014
2020/0323422 A1* 10/2020 Duan ................. A61B 1/00128
2021/0060296 A1* 3/2021 Velis ...................... A61B 5/015
2021/0267438 A1* 9/2021 Velis ................. A61B 1/00006

* cited by examiner

ENDOSCOPE DEVICE AND ENDOSCOPIC DETECTION METHOD

CROSS-REFERENCE OF RELATED APPLICATIONS

The application claims priority to Chinese Patent Application No. 201810879377.7 filed on Aug. 3, 2018, the contents of which are incorporated by reference herein.

FIELD OF INVENTION

The present invention relates to the field of medical device, and in particular, to an endoscope apparatus and an endoscopic detection method.

BACKGROUND

With the continuous development of medical technologies, the application range of endoscope has become increasingly extensive. The endoscope can enter the body of the subject (for example, the esophagus) to take images of regions to be examined, so as to determine whether lesions exist at the regions.

Since the endoscope needs to be placed in the body of the subject, the subject may experience discomfort during the examination. In order to alleviate the discomfort, a capsule endoscope has become smaller and smaller in size. Taking the esophageal examination as an example, the subject can swallow the capsule endoscope such that the capsule endoscope enters the esophagus and slowly moves while taking images of the esophagus.

However, the capsule endoscope usually stays in the esophagus of the subject for a very short period of time, which results in that the capsule endoscope can only take few images, thus causing missed detection. Therefore, the conventional capsule endoscope has a problem that the lesion detection accuracy is low.

SUMMARY OF THE INVENTION

The present invention discloses an endoscope apparatus and endoscopic detection method to improve detection accuracy.

The present invention provides an endoscope apparatus, which comprises:
a release source;
a tether connected to the release source;
an elastic clamp member; wherein the elastic clamp member comprises an elastic clamp cavity, and the elastic clamp cavity is interconnected to an air outlet of the release source through the tether;
a capsule endoscope;
wherein the capsule endoscope and the elastic clamp member are configured as: in a clamped state, at least a portion of the capsule endoscope is within the elastic clamp cavity, the elastic clamp member has an ability to recover from deformation to apply a clamping force to the capsule endoscope; in a released state, the elastic clamp member is expanded by the air pressure from the tether, and the capsule endoscope is released from the elastic clamp cavity.

Optionally, one end of the tether connected to the elastic clamp member set as a spiral structure, and the spiral structure forms a capsule accommodating cavity, the capsule accommodating cavity is connected and placed in close proximity to the elastic clamp cavity; the spiral structure gradually unwinds with the movement of the capsule endoscope in the clamped state.

Optionally, the spiral structure is shaped by edible hydrosol.

Optionally, a middle section of the capsule endoscope is a cylindrical section, the spiral structure is sleeved on the cylindrical section, and the spiral structure and the elastic clamp member are spaced apart.

Optionally, the inner diameter of the spiral structure is greater than or equal to the outer diameter of the cylindrical section, and the difference between the inner diameter and the outer diameter is 0 to 1 mm.

Optionally, the last turn of the spiral structure is closer to the air inlet of the elastic clamp member than the first turn of the spiral structure.

Optionally, the first turn of the spiral structure is closer to the air inlet of the elastic clamp member than the last turn of the spiral structure, and the portion of the tether between the last turn and the air inlet is located inside the spiral structure.

Optionally, the portion of the tether connected to the first turn is a U-shaped-curvature structure, and the bent portion of the U-shaped-curvature structure is located inside the last turn of the tether.

Optionally, the elastic clamp member comprises a spherical inner wall, and the maximum lateral diameter of the spherical inner wall is a first diameter and the maximum lateral diameter of the portion of the capsule endoscope in contact with the spherical inner wall is a second diameter; wherein the first diameter is smaller than the second diameter, the first diameter is 5 to 9 mm, and the second diameter is 9 to 20 mm.

Optionally, the elastic clamping member and the capsule endoscope are set as: in the clamped state, the ratio between the volume of the portion of the capsule endoscope in the elastic clamp cavity and the total volume of the capsule endoscope is between 1/5 and 1/2.

Optionally, the endoscope apparatus further comprises a control system, wherein the capsule endoscope comprises a magnet unit, and the control system controls the orientation of the capsule endoscope by the magnet unit. An example of the control system can be found in Applicants' U.S. application Ser. No. 14/486,061, which is an external magnetic control assembly comprising essentially a magnetic ball and mechanical arms.

Optionally, the tether is integrally formed with the elastic clamp member, and the tether and the elastic clamp member are made of different materials.

Optionally, the tether comprises scale marks.

The present invention provides an endoscopic detection method that comprises the following steps:
step S1: under a normal pressure, insert at least a portion of the capsule endoscope into the elastic clamp cavity, wherein the elastic clamp member has an ability to recover from deformation to apply a clamping force to the capsule endoscope;
step S2: place the capsule endoscope and the elastic clamp member into a target position under the traction of the tether;
step S3. inject air into the elastic clamp cavity by the release source until the elastic clamp member is expanded by the air pressure, so that the capsule endoscope is released from the elastic clamp cavity.

Optionally, the endoscopic method further comprises the following steps before the step S1:
wind the tether around the capsule endoscope from the end connected to the elastic clamp member to form a spiral structure that gradually unwinds with the movement of the capsule endoscope in a clamped state, wherein the inner side of the spiral structure forms a capsule accommodating cavity that is connected and placed in close proximity to the elastic clamp cavity.

The present invention can achieve the following beneficial effects:

the endoscope apparatus as disclosed herein uses a tether to connect to an elastic clamp member, and the elastic clamp member can clamp the capsule endoscope, so that the tether is always connected to the capsule endoscope as the later moves through the digestive tract of the subject. The operator can control the state of motion of the capsule endoscope with the tether, to extend retention time of the capsule in the body of the subject, thereby preventing missed detection and improving detection accuracy. In addition, when the capsule endoscope is inserted into the elastic clamp member, the elastic clamp member can inflate and deform to apply a clamping force to the capsule endoscope, which is more reliable and prevents the capsule from being detached from the elastic clamp member due to insufficient force, thereby more reliably extending the time during which the capsule endoscope stays in the subject.

It should be understood that the above general description and the following detailed description are merely exemplary and are not intended to limit the invention.

Figure 1:
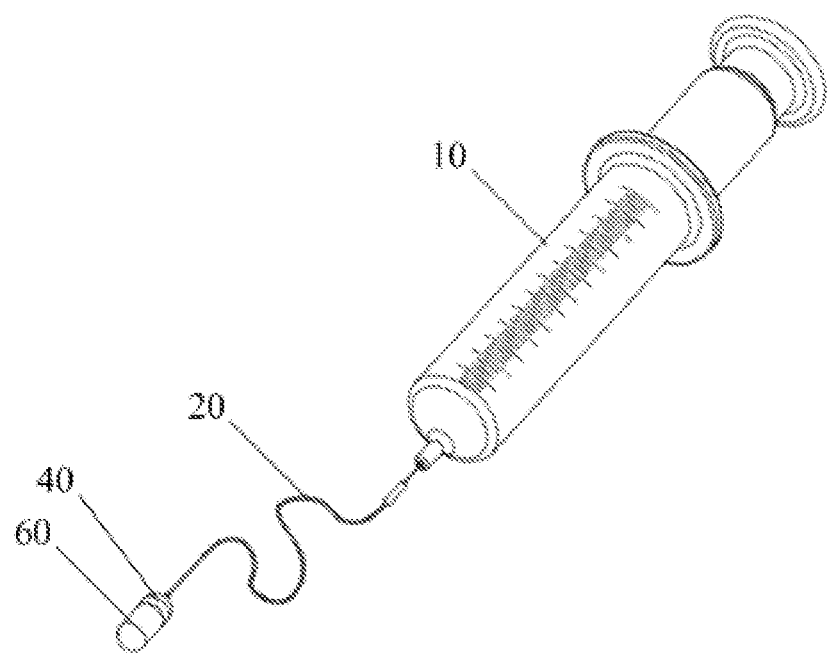
FIG. 1 shows a schematic view of a first embodiment of an endoscope apparatus according to the present invention.
Figure 2:
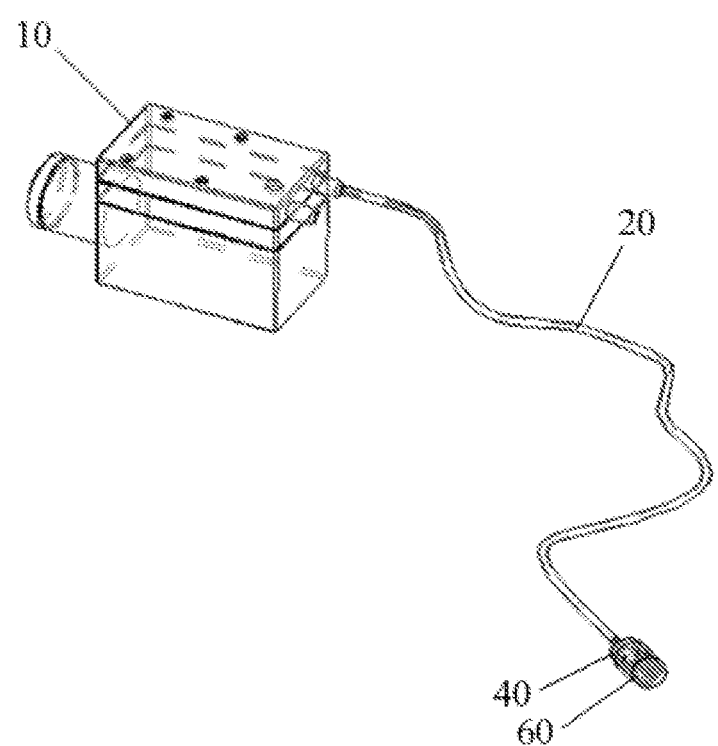
FIG. 2 shows a schematic view of a second embodiment of an endoscope apparatus according to the present invention.

Elements in the drawings are:
10—Release source
20—Tether
21—Spiral structure
40—Elastic clamp member
41—Elastic clamp cavity
60—Capsule endoscope
601—Spherical end
602—Cylindrical section
61—Optical transparent cover
62—Illumination array
63—Lens
64—Image sensor
65—Microprocessor
66—Magnet unit
67—Battery
68—radio frequency transceiver module
69—Transceiver antenna
610—Capsule enclosure
70—Control system The drawings herein are incorporated in and constitute a part of the specification, illustrate the embodiments consistent with the invention and are used together with the specification to explain the principles of the invention.

DETAILED DESCRIPTION

In order to make the objects, technical solutions, and advantages of the present invention more understandable, the present invention can be further described in detail below with reference to the accompanying drawings and embodiments. It is understood that the embodiments described herein are merely illustrative of the invention and are not construed as limited to the invention.

In the description of the present invention, unless otherwise specified or defined, the term "multiple" means two or more. Unless otherwise specified or stated, the terms "connection", "fixing", etc. shall be understood in a broad sense, for example, the "connection" may be a fixed connection, a detachable connection, or an integral connection, or an electrical connection. It may be a direct connection or indirection connection through an intermediate medium. For those skilled in the art, the specific meanings of the terms in the present invention can be understood on a case-by-case basis.

Referring to FIGS. 1-5, the present invention provides an endoscope apparatus. The endoscope apparatus can be used to examine a target position in the body of a subject to determine whether lesions exist. For example, the endoscope apparatus can examine whether there are lesions in the esophagus of the subject. The following describes the endoscope apparatus by taking this implementation as an example.

Figure 17:
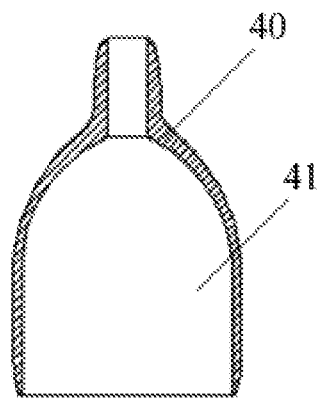
FIG. 17 shows a sectional view of the elastic clamp member as shown in FIG. 16.

The endoscope apparatus comprises a release source 10, a tether 20, an elastic clamp member 40 and a capsule endoscope 60. The release source 10 can output air to generate an appropriate acting force. For example, the release source 10 can be a syringe (as shown in FIG. 1) or an air injection pump (shown in FIG. 2). The release source 10 comprises an air outlet. The tether 20 is connected to the release source 10. One end of the tether 20 is connected to the air outlet of the release source 10, so that the air output from the release source 10 can enter the tether 20. The tether 20 can be a flexible tube that can be made of non-toxic materials with stable properties, such as biocompatible silicone, to ensure its safety. In addition, the outer diameter of the tether 20 can be set to 0.5~1.5 mm to ensure that the tether 20 does not produce too strong a sensation of a foreign body in throat, and cannot cut the esophagus. The elastic clamp member 40 can be made of biocompatible silicone, and the wall thickness can be set to 0.1-0.5 mm. The elastic clamp member 40 has elasticity which leads to an elastic deformation as a force is applied on it. In one embodiment, the elastic clamp member 40 can produce an ability to contract and expand, and comprises an elastic clamp cavity 41 (refer to FIG. 17). The elastic clamp cavity 41 is interconnected to the air outlet of the release source 10 through the tether 20. The elastic clamp member 40 and the tether 20 can be integrally formed to ensure air tightness, and can be made of different materials to ensure flexibility in materials selection according to the functions of the elastic clamp member 40 and the tether 20, so as to optimize their effects. Also, the elastic clamp member 40 and the tether 20 can be connected by bonding. That is, the other end of the tether 20 is connected to the elastic clamp member 40 so that the air output from the release source 10 can flow into the elastic clamp cavity 41 through the tether 20.

The capsule endoscope 60 is a core unit of the endoscope apparatus, which can enter the esophagus of the subject and move along the esophagus. While the capsule endoscope 60 moves, the capsule endoscope 60 takes images of the esophagus, and whether lesions exist in the esophagus of the subject is determining according to the images. In addition, the posture of the capsule endoscope 60 in the esophagus can be adjusted to adjust the viewing angle. In one embodiment, the viewing angle of the capsule endoscope 60 in the esophagus can adjust by rotating or swinging of mechanical structure of the capsule endoscope 60. In another embodiment, the viewing angle of the capsule endoscope 60 in the esophagus can adjust by an external control system.

Figure 3:
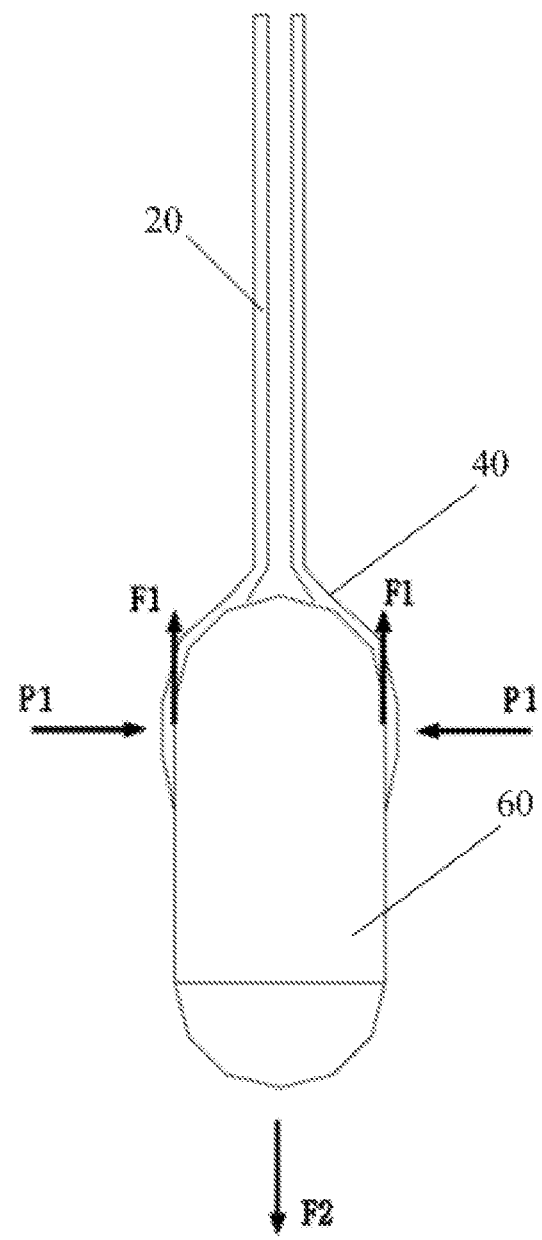
FIG. 3 shows a schematic view of a partial structure of a capsule endoscope device in a clamped state according to the present invention.

The elastic clamp member 40 and the capsule endoscope 60 are configured to:

Configuration A: As shown in FIG. 3, in a clamped state, at least a portion of the capsule endoscope 60 is within the elastic clamp cavity 41, and the elastic clamp member 40 is expanded by the capsule endoscope 60 and thus has an ability to recover from deformation to apply a clamping force P1 to the capsule endoscope 60. Under the action of the clamping force P1, a friction F1 is generated on the contact between the elastic clamp member 40 and the capsule endoscope 60 while a discharge force F2 generated by compression of esophageal muscle is applied onto the capsule endoscope 60. F1>F2, the capsule endoscope 60 is firmly clamped by the elastic clamp member 40, and movement of the capsule endoscope 60 limits by the tether 20.

Figure 4:
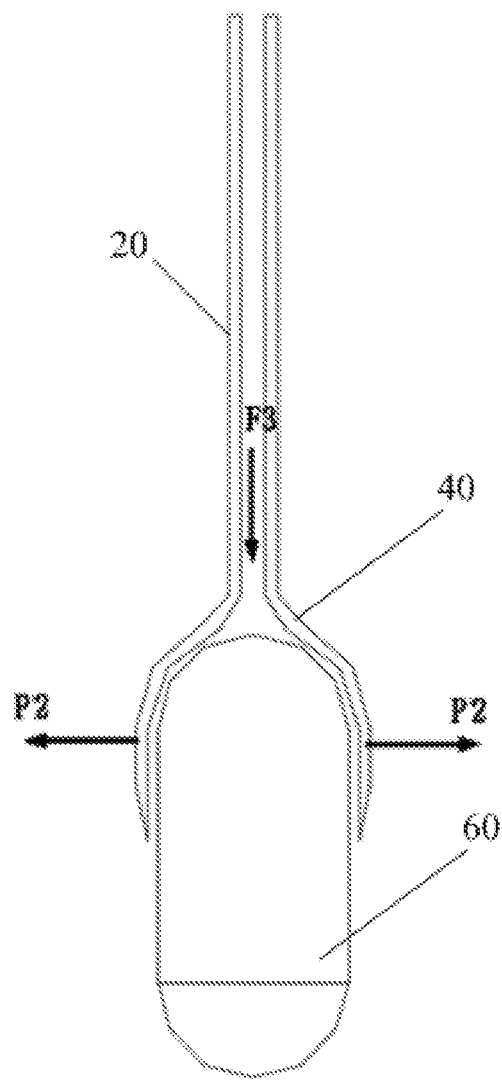
FIG. 4 shows a schematic view of a partial structure of a capsule endoscope device in a released state according to the present invention.

Configuration B: When the capsule endoscope 60 completes detection, the capsule endoscope 60 is released to facilitate discharge. As shown in FIG. 4, in a released state, the release source 10 injects air into the elastic clamp cavity 41 through the tether 20. Since the elastic clamp member 40 is tightly attached to the capsule endoscope 60, the pressure P2 in the elastic clamp cavity 41 can gradually increase, and when the pressure P2 reaches a certain value, the elastic clamp member 40 can expand to release the capsule endoscope 60. That is, the elastic clamp member 40 is expanded under the pressure of air through the tether 20, and then the capsule endoscope 60 is no longer restrained by the elastic clamp member 40. The air can apply a pushing force F3 to the capsule endoscope 60, and under the pushing force F3, the capsule endoscope 60 can be released from the elastic clamp cavity 41.

As described above, the endoscope apparatus comprises the tether 20 in connection with the elastic clamp member 40, and the elastic clamp member 40 can clamp the capsule endoscope 60, so that the tether 20 is always connected to the capsule endoscope 60 as the capsule endoscope 60 moves inside the esophagus of the subject. The motion of the capsule endoscope 60 can be controlled by an operator through the tether 20, to extend retention time of the capsule endoscope 60 in the esophagus of the subject, thereby preventing missed detection and improving detection accuracy. In addition, when the capsule endoscope 60 is placed in the elastic clamp member 40, the elastic clamp member 40 can be inflated and deformed to apply a clamping force to the capsule endoscope 60, which is more reliable and prevents the capsule endoscope 60 from being detached from the elastic clamp member 40 due to insufficient force, thereby more reliably extending the time during which the capsule endoscope stays in the esophagus of the subject.

Figure 5:
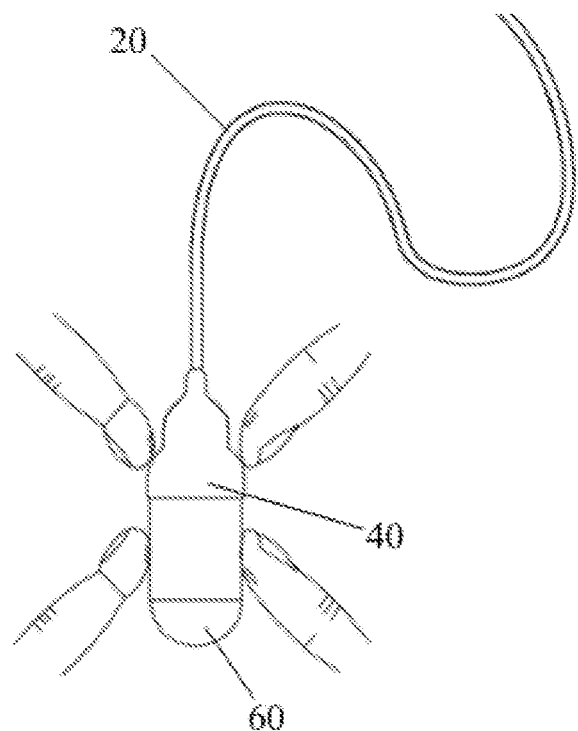
FIG. 5 shows a schematic view of a method of assembling the capsule endoscope according to the present invention.
Figure 6:
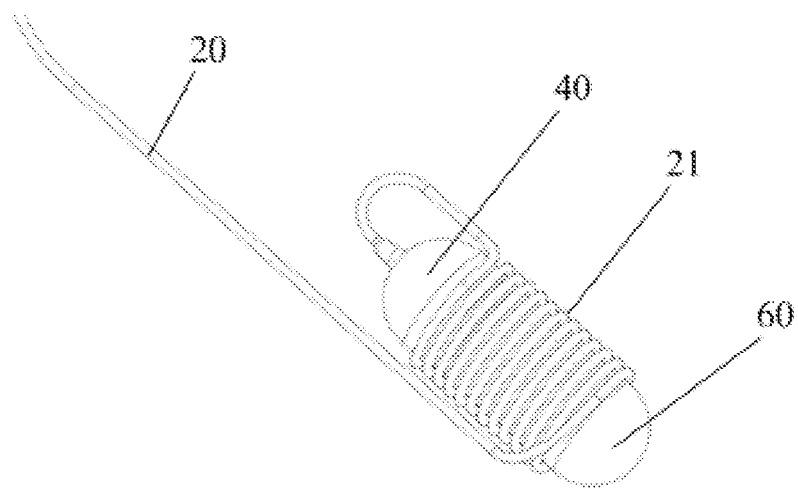
FIG. 6 shows a schematic view of a partial structure of an endoscope apparatus according to a third embodiment of the present invention.
Figure 7:
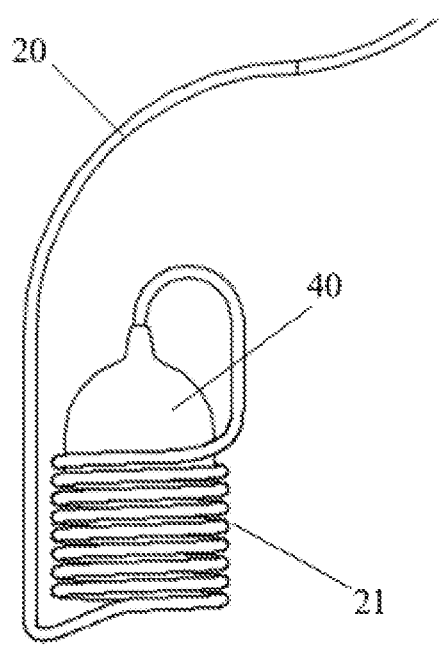
FIG. 7 shows a schematic view of a connection state of a tether and an elastic clamp member as shown in FIG. 6.
Figure 8:
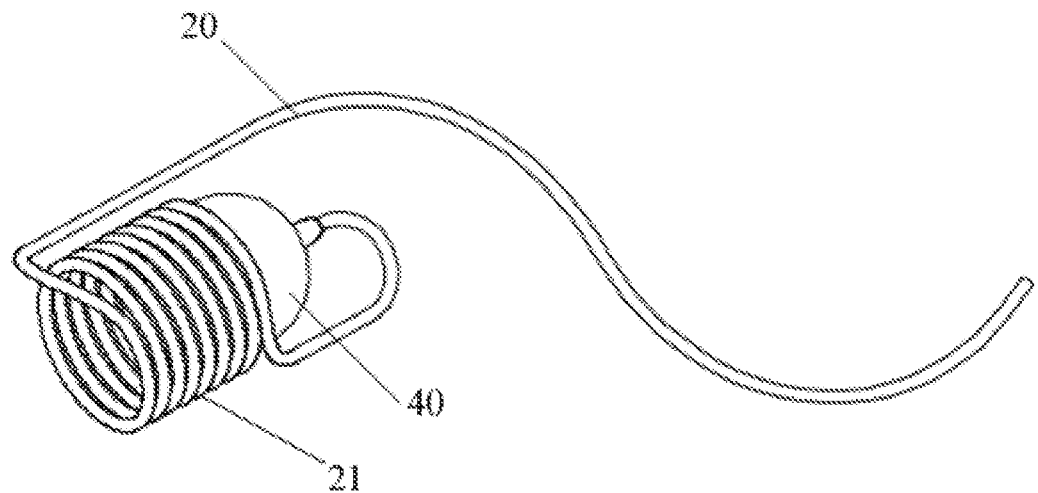
FIG. 8 shows a schematic view of the structure shown in FIG. 7 from other viewing angle.
Figure 9:
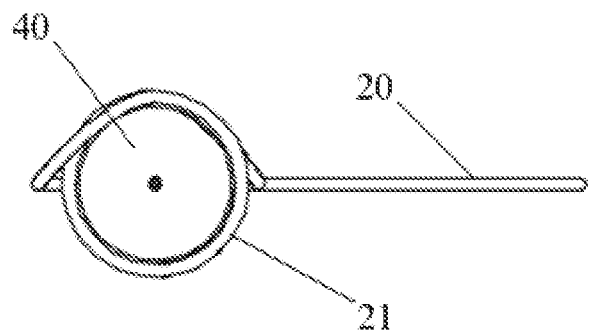
FIG. 9 shows a bottom view of the structure shown in FIG. 7.

There is a plurality of methods to insert the capsule endoscope 60 into the elastic clamp member 40. One method is provided as follows:

As shown in FIG. 5, the elastic clamp member 40 is held by one hand, the capsule endoscope 60 is held by another hand, and the capsule endoscope 60 is carried close to the elastic clamp member 40. When the capsule endoscope 60 gets in touch with the elastic clamp member 40, a pushing force from the corresponding hand is applied to the capsule endoscope 60 and is transmitted to the elastic clamp member 40. The pushing force can expand the elastic clamp member 40 until a portion of the capsule endoscope 60 enters the elastic clamp cavity 41, and at this point the elastic clamp member 40 applies a clamping force to the capsule endoscope 60.

Figure 10:
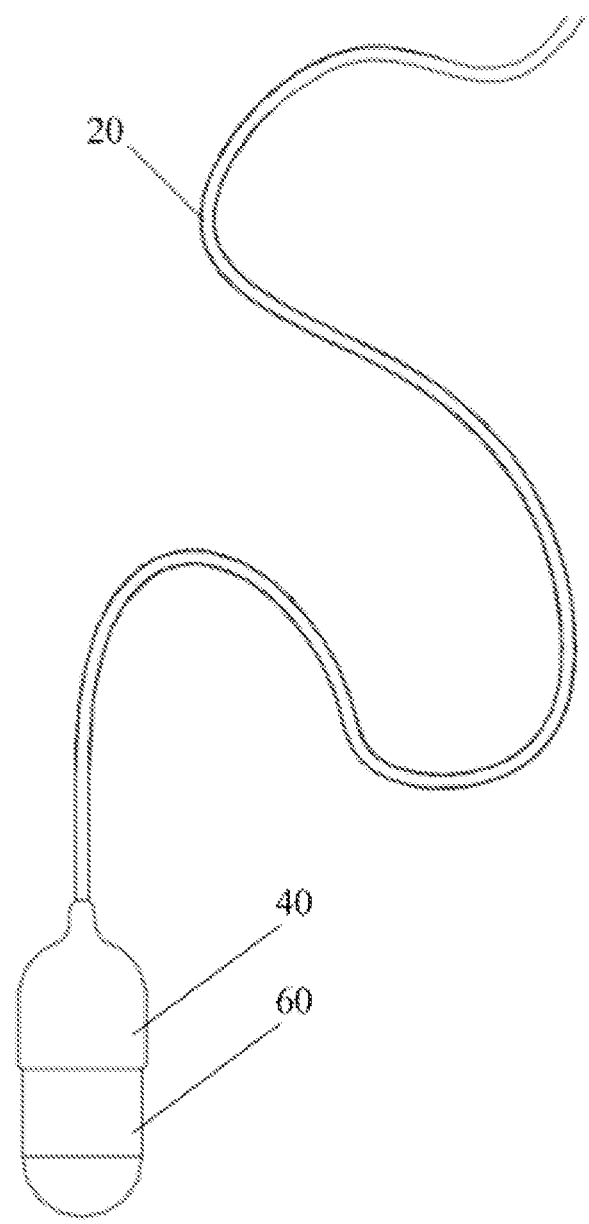
FIG. 10 shows a schematic view of the structure shown in FIG. 6 with the tether unwound.
Figure 11:
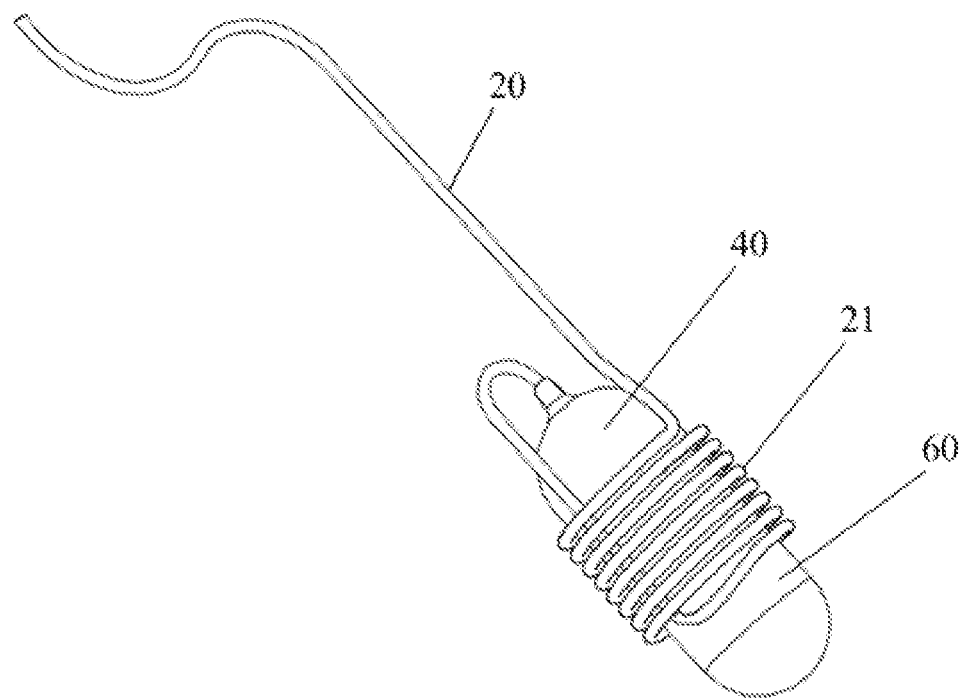
FIG. 11 shows a schematic view of a partial structure of an endoscope apparatus according to a fourth embodiment of the present invention.
Figure 12:
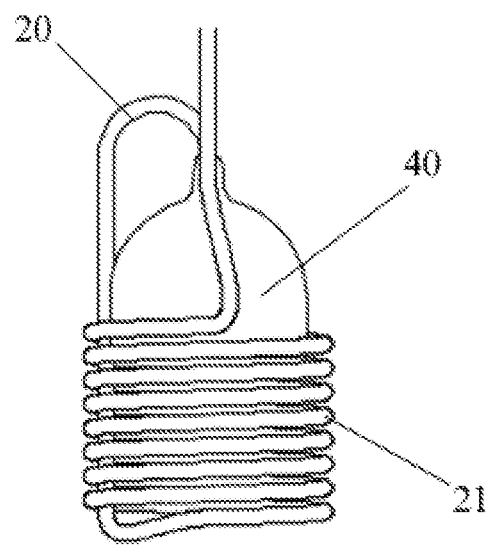
FIG. 12 shows a schematic view of a connection state of a tether and an elastic clamp member as shown in FIG. 11.
Figure 13:
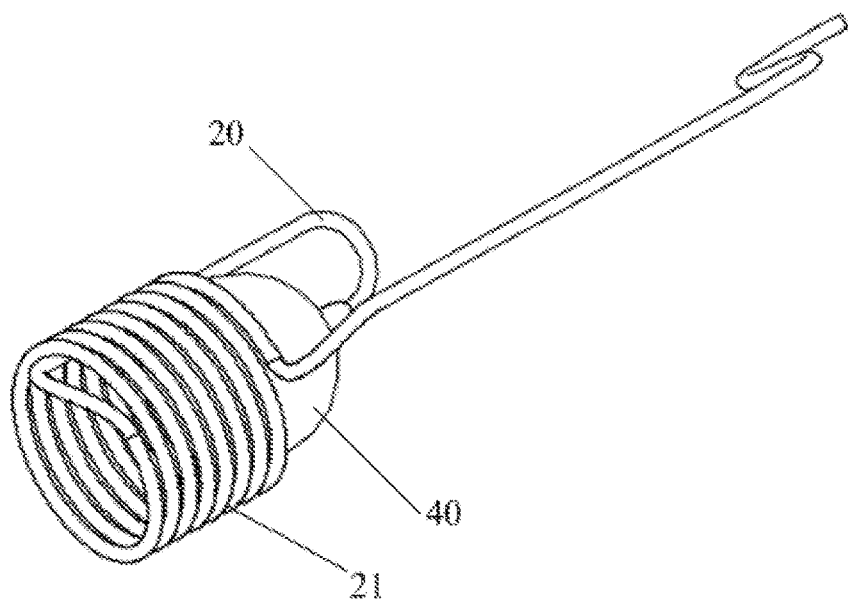
FIG. 13 shows a schematic view of the structure shown in FIG. 12 from other viewing angle.
Figure 14:
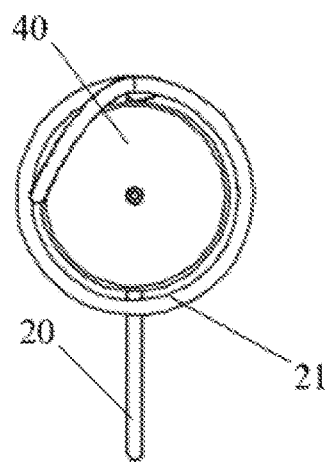
FIG. 14 shows a bottom view of the structure shown in FIG. 12.

In a further embodiment, as shown in FIG. 6-9, one end of the tether 20 connected to the elastic clamp member 40 can be set as a spiral structure 21. The number of turns of tether winding around the capsule, which forms the spiral structure 21. The number of turns of the spiral structure 21 can be 5 to 10, and the inner diameter of each turn can be equal. The inner side of the spiral structure 21 forms a capsule accommodating cavity that is connected and placed in close proximity to the elastic clamp cavity 41 of the elastic clamp member 40. That is, after the capsule endoscope 60 is inserted into the elastic clamp cavity 41, it is also in the capsule accommodating cavity of the spiral structure 21. The clamped state of the spiral structure 21 is set to gradually unwind with the movement of the capsule endoscope 60. That is, when the capsule endoscope 60 slowly moves in the esophagus while taking images, the spiral structure 21 can gradually unwind, and the fully unwound structure is shown as FIG. 10.

The spiral structure 21 as described above can extend the traction range of the tether 20, ensuring that the operator does not need to repeatedly pull the tether 20 after the capsule endoscope 60 is swallowed by the subject, so that no obvious foreign body sensation can be felt by the subject. The tether 20 is also gradually unwound, which can generate a certain buffering for the movement of the capsule endoscope 60, and thereby avoid discomfort brought to the subject when the length of the tether 20 reaches the limit and the capsule endoscope 60 abruptly stops. Therefore, this spiral structure 21 can bring a better examination experience.

There is a plurality of ways to realize a slow unwinding of the tether 20. For example, the tether 20 can be flexible based on selection of material, so that the flexible tether can be wound around the capsule endoscope 60 to form the spiral structure 21 and be unwound slowly under the compression of esophagus. However, in order to more precisely control the shape of the tether 20, in a preferred embodiment, edible hydrosol is used to shape the spiral structure 21. That is, before the capsule endoscope 60 enters the esophagus, the turns of the spiral structure 21 are bonded by edible hydrosol, so that the spiral structure 21 maintains its spiral shape. After the capsule endoscope 60 is swallowed into the esophagus, the liquid in the esophagus is in contact with the edible hydrosol, making the edible hydrosol slowly melted, and therewith the spiral structure 21 gradually unwinds.

The edible hydrosol can be gelatin, etc.

Figure 15:
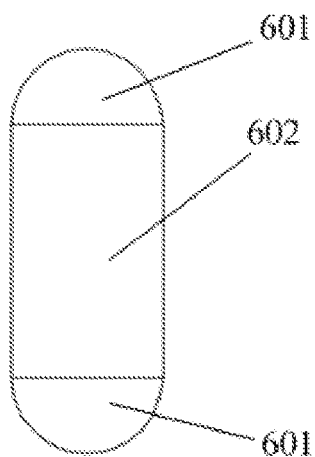
FIG. 15 shows a schematic view of a capsule endoscope according to the present invention.
Figure 16:
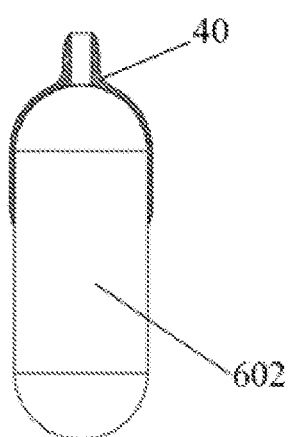
FIG. 16 shows a schematic view of a connection state of an elastic clamp member and the capsule endoscope as shown in FIG. 15.

As shown in FIG. 15, both ends of the capsule endoscope 60 can be set as a spherical structure 601, and the middle section can be set as a cylindrical section 602. As shown in FIG. 16, the elastic clamp member 40 can accommodate the spherical structure 601, and can even extend to a portion of the cylindrical section 602 to enlarge contact area between the elastic clamp member 40 and the capsule endoscope 60 to improve clamping effect. The contact area between the elastic clamp member 40 and the cylindrical section 602 can be 0 to 10 mm. The spiral structure 21 can be sleeved on the cylindrical section 602, and the spiral structure 21 and the elastic clamp member 40 are spaced apart. That is, the spiral structure 21 and the elastic clamp member 40 are not in contact with each other, so that the process of gradual unwinding of the spiral structure 21 is not affected by the elastic clamp member 40, ensuring the smoothness of the whole process of unwinding and improving the feeling of the subject during examination.

When the spiral structure 21 is in contact with the capsule endoscope 60 and has a pressure on the capsule endoscope 60, unwinding of the spiral structure 21 can be hindered by the capsule endoscope 60. When the spiral structure 21 is not in contact with the capsule endoscope 60, such hindering effect will be reduced, but if the space between the spiral structure 21 and the capsule endoscope 60 is large, the spiral structure 21 may unwind untimely and too fast, causing discomfort to the subject. In view of this, in an alternative embodiment, the inner diameter of the spiral structure 21 is greater than or equal to the outer diameter of the cylindrical section 602, and the difference between the spiral structure 21 and the capsule endoscope 60 is 0 to 1 mm, so that the timing and speed of unwinding of the spiral structure 21 are more appropriate, and the subject can have a better examination experience.

Figure 21:
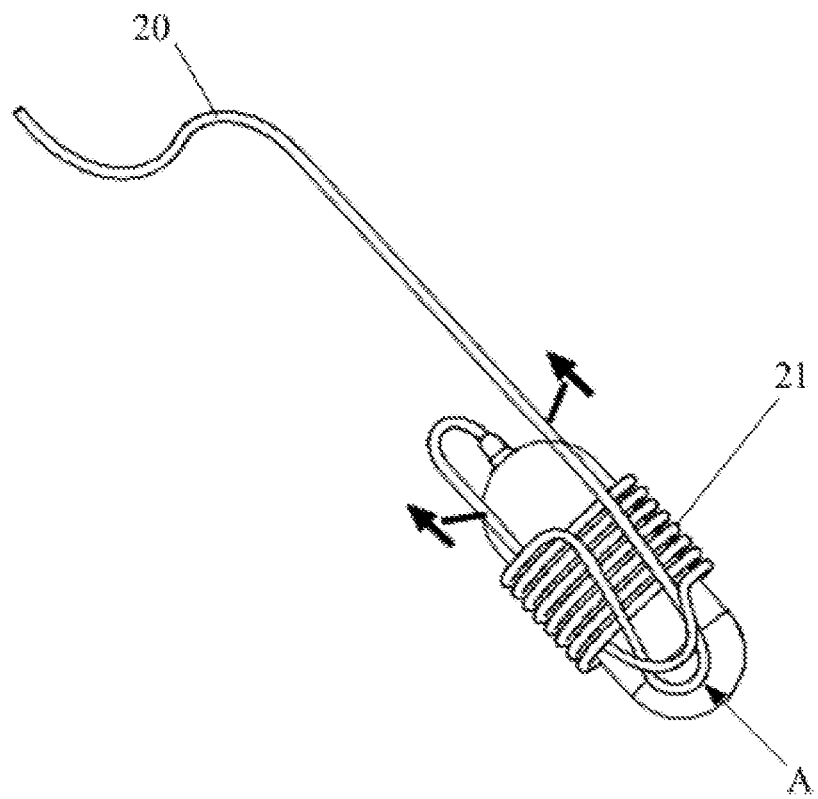
FIG. 21 shows a schematic view an initial state of a tether and an elastic clamp member of the endoscope apparatus according to fifth embodiment of the present invention.
Figure 22:
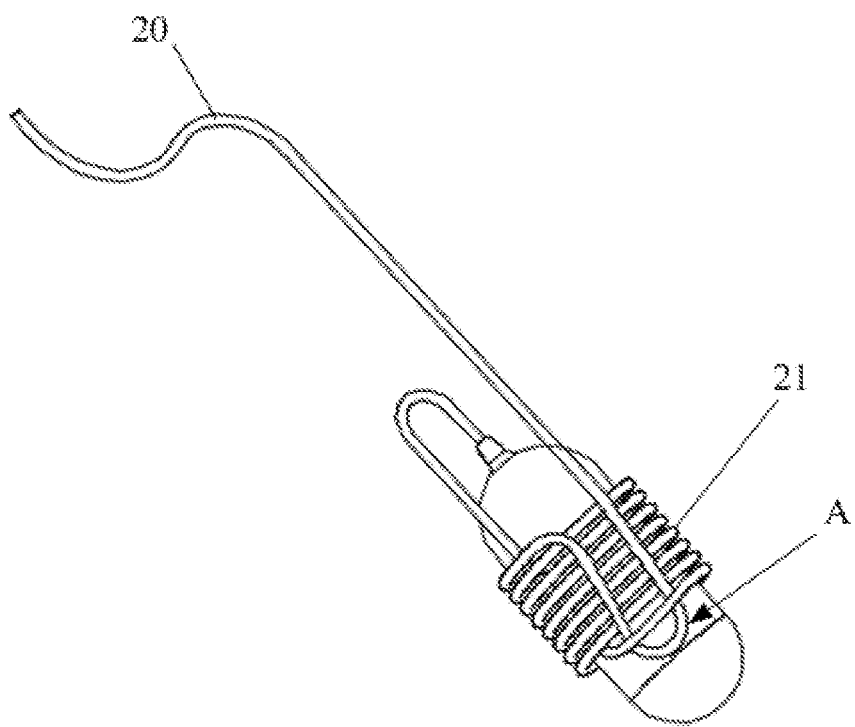
FIG. 22 shows a schematic view of a tightened state of the tether and elastic clamp member as shown in FIG. 21.

For the winding direction of the spiral structure 21, there are two ways described as follow. First, as shown in FIGS. 11-14, the first turn of the spiral structure 21 is closer to the air inlet of the elastic clamp member 40 than the last turn of the spiral structure 21, and the portion of the tether 20 from the last turn to the air inlet of the elastic clamp member 40 is located inside the spiral structure 21, which is more conducive to unwind the spiral structure 21. The air inlet of the elastic clamp member 40 is the end of the elastic clamp member 40 connected to the tether 20. Second, as shown in FIGS. 6-9, the last turn of the spiral structure 21 is closer to the air inlet of the elastic clamp member 40 than the first turn of the spiral structure 21, which is more convenient for winding spiral structure 21. Optionally, for the second way, as shown in FIG. 21 and FIG. 22, the portion of the tether 20 connected to the first turn is a U-shaped-curvature structure, and the bent portion A of the U-shaped-curvature structure is located inside the last turn of the tether 20. The U-shaped-curvature structure in an initial state is as shown in FIG. 21, and a tightened state of the U-shaped-curvature structure as shown in FIG. 22 can be obtained by pulling the tether 20 in the direction indicated by the arrow in FIG. 21.

As described above, the two ends of the capsule endoscope 60 are configured as a spherical structure 601. Therefore, the inner wall of the elastic clamp member 40 is correspondingly configured as a spherical shape. The maximum lateral diameter of the spherical inner wall of the elastic clamp member 40 in the natural state is a first diameter and the maximum lateral diameter of the portion of the capsule endoscope 60 in contact with the spherical inner wall (the spherical structure 601) is a second diameter. The first diameter is smaller than the second diameter, the first diameter is 5 to 9 mm, and the second diameter is 9 to 20 mm. The first diameter is the largest diameter of the spherical inner wall of the elastic clamp member 40 in its own cross section, and the second diameter is the maximum diameter of the capsule endoscope 60 in its own cross section. The first diameter is smaller than the second diameter, so that the capsule endoscope 60 can expand the elastic clamp member 40, which in turn produces a clamping force between the capsule endoscope 60 and the elastic clamp member 40, and a proper clamping force can be produced when the first and second diameters are within the aforementioned range of values.

As can be seen from the foregoing description, the magnitude of the force between the elastic clamp member 40 and the capsule endoscope 60 is directly determined by the contact area between the two. Therefore, in an embodiment, in order to make the force moderate, the elastic clamp member 40 and the capsule endoscope 60 are configured as: in the clamped state, the ratio between the volume of the portion of the capsule endoscope 60 inside the elastic clamp cavity 41 and the total volume of the capsule endoscope 60 is ⅕~½. Making the force moderate means that the elastic clamp member 40 can not only firmly clamp the capsule endoscope 60 in the clamped state but also conveniently release the capsule endoscope 60 in the released state.

Figure 18:
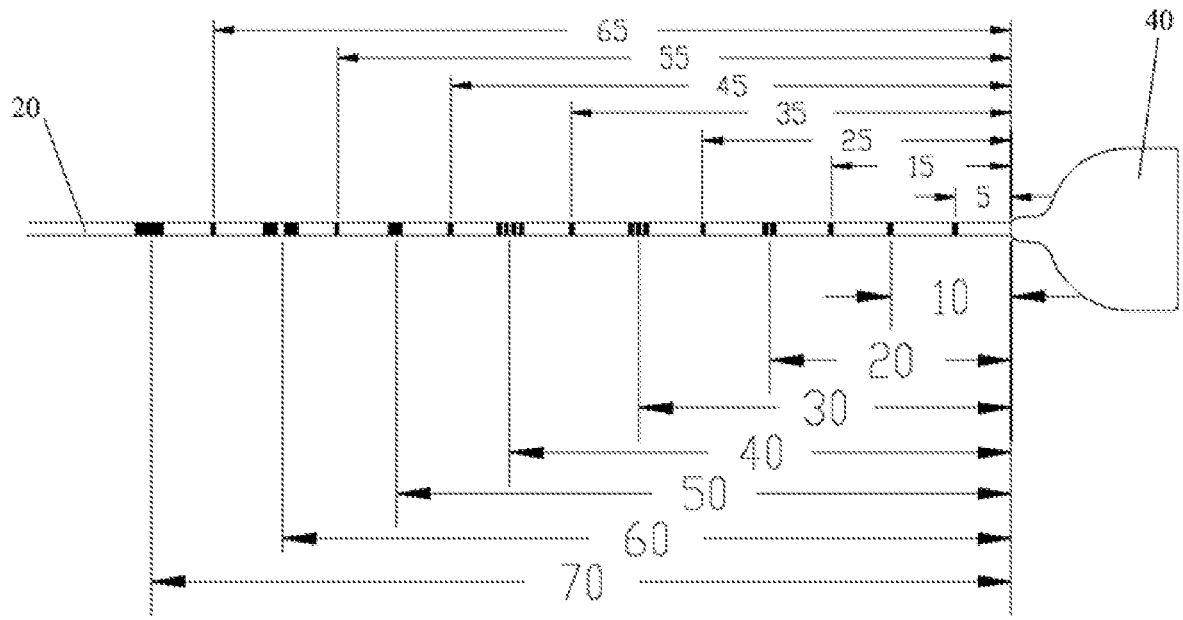
FIG. 18 shows a schematic view of a partial structure of the tether of an endoscope apparatus according to the present invention.
Figure 19:
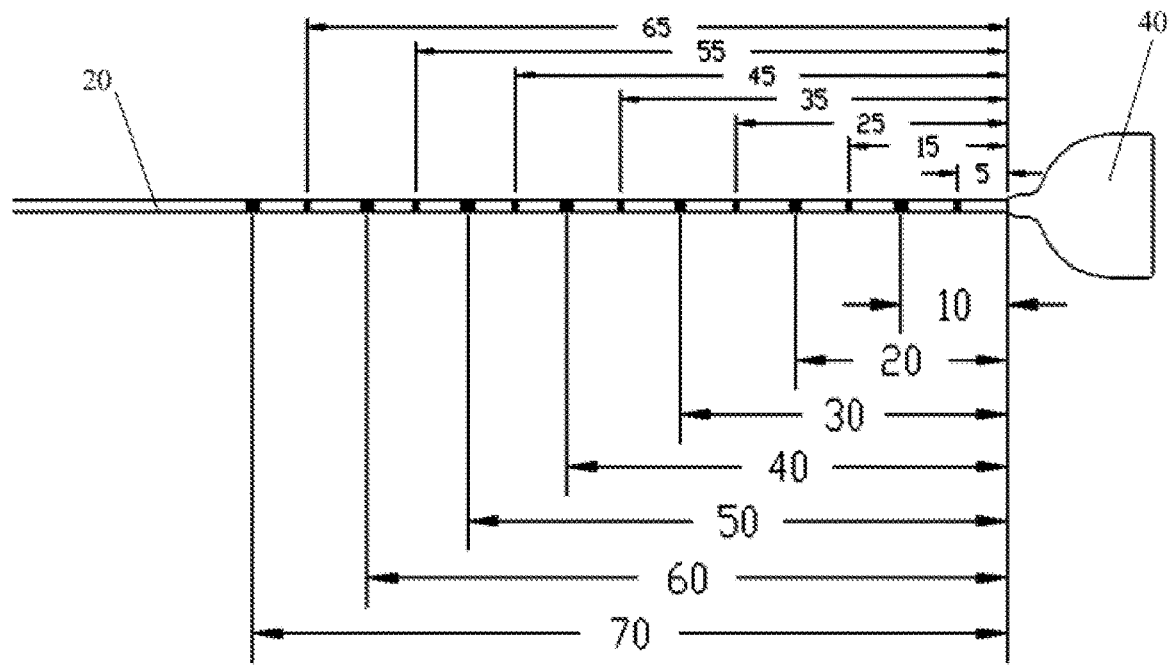
FIG. 19 shows another schematic view of a partial structure of the tether of the endoscope apparatus according to the present invention.

In order to make it easier to determine the position of a lesion in the esophagus, scale marks can be made on the tether 20, and the distance between the lesion and the oral cavity can be determined according to the scale marks. Specifically, as shown in FIG. 18 and FIG. 19, the scale marks on the tether 20 are divided into a first scale mark and a second scale mark, wherein the length represented by the first scale mark is a multiple of 5 and the length represented by the second scale mark is a multiple of 10. The unit of the length represented by the scale marks shown in FIG. 18 and FIG. 19 can be cm. In the structure shown in FIG. 18, the structural features of the first scale marks can be the same, and the structural features of the second scale marks can be different. For example, different numbers of lines can be set according to the specific length represented. In the structure shown in FIG. 19, the structural features of the first scale marks are the same, and the structural features of the second scale marks are also the same, but the structural features between the first scale marks and the second scale marks are different. The structural features make the operator more easily to recognize the scale mark and determine the lesion position, while the lengths represented by the scale marks are unrecognizable since the tether 20 is small in size. In other embodiment, the first scale marks and the second scale marks can be distinguished by colors.

Figure 20:
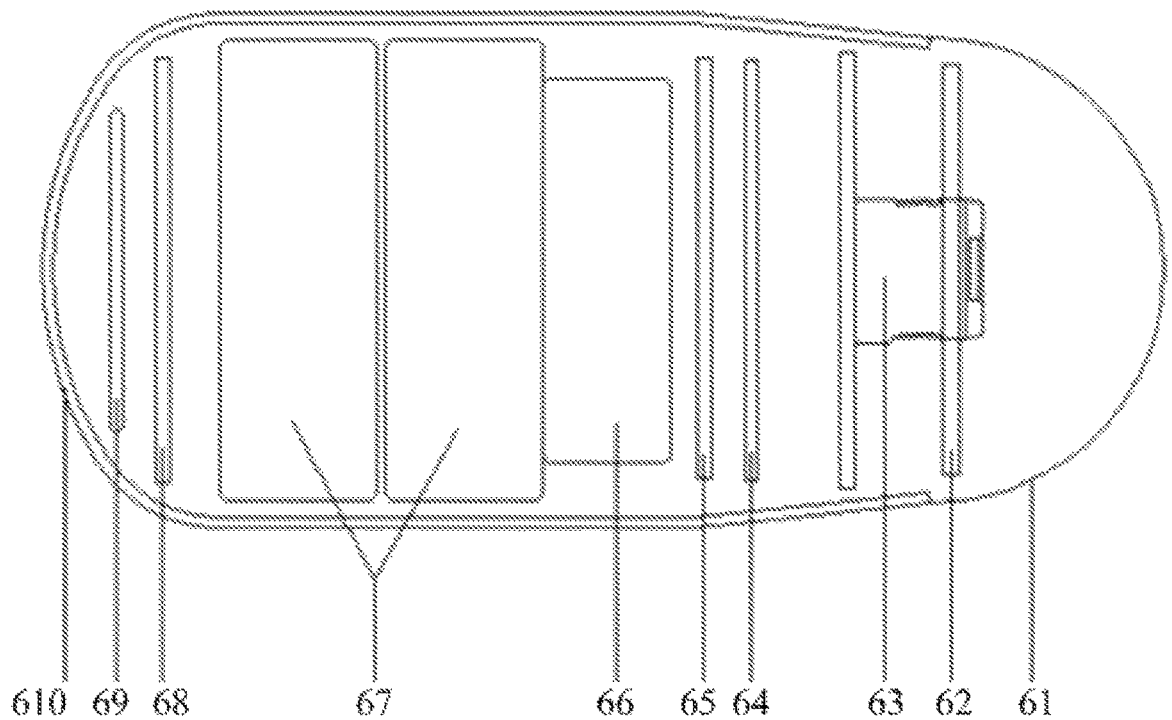
FIG. 20 shows a perspective view of the capsule endoscope according to the present invention.

As described above, the present invention provides a device that can control the moving speed of the capsule endoscope 60 by pulling, and the posture of the capsule endoscope 60 can be adjusted. To achieve this, in the embodiment, the capsule endoscope 60 comprises constituter components as shown in FIG. 20. Specifically, the capsule endoscope 60 comprises an optical transparent cover 61, an illumination array 62, a lens 63, an image sensor 64, a microprocessor 65, a magnet unit 66, a battery 67, a radio frequency transceiver module 68, a transceiver antenna 69 and a capsule enclosure 610. The optical transparent cover 61 and the capsule enclosure 610 form an accommodation enclosure where the remaining constituter components are disposed. The illumination array 62, the lens 63, the image sensor 64, and the microprocessor 65 are used for capturing images and processing the images. The radio frequency transceiver module 68 and the transceiver antenna 69 are used for data transmission, and the battery 67 provides power supply for the capsule endoscope 60. The magnet unit 66 can be a permanent magnet or a magnetic dipole. In one embodiment, the endoscope apparatus may further comprise a control system including a portion that can interact with the magnet unit 66, thereby controlling the orientation of the capsule endoscope 60 by the magnet unit 66. In one embodiment, the endoscope apparatus further comprises sensors for measuring external magnetic field and transmitting data to an external device in a wireless manner. The control system can synthesize internal data of the capsule endoscope 60 and real-time distribution of the external magnetic field, to determine the position and orientation of the capsule endoscope 60 in the human body in real time for subsequent control.

Figure 23:
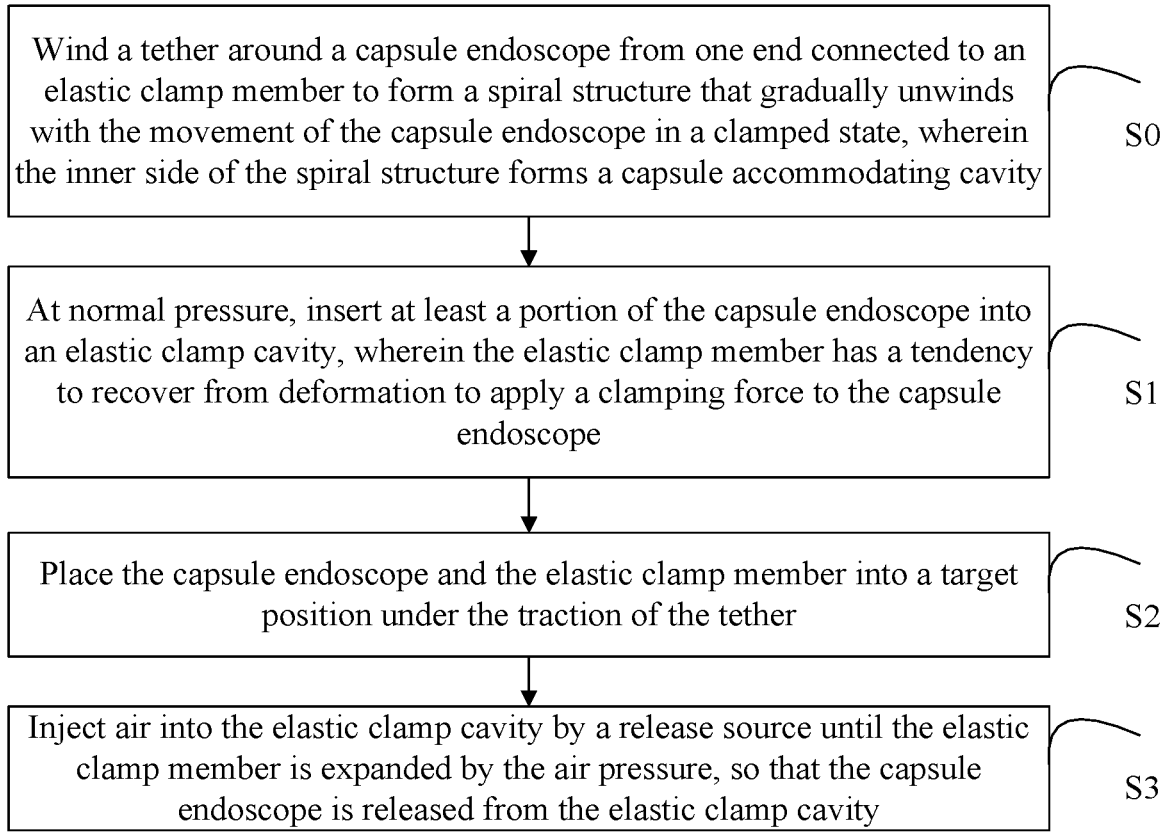
FIG. 23 shows a flowchart of an endoscopic detection method according to the present invention.

Based on the above structure, the present invention further provides an endoscopic detection method, which is applied to the endoscope apparatus according to any of the above embodiments. As shown in FIG. 23, the method includes the following steps.

Step S1: At normal pressure, at least a portion of the capsule endoscope 60 is inserted in the elastic clamp cavity 41. At this point, the elastic clamp member 40 has an ability to recover from deformation, thus to apply a clamping force to the capsule endoscope 60.

Step S2: The capsule endoscope 60 and the elastic clamp member 40 are placed into a target position under the traction of the tether 20. The target position can be the esophagus of the subject, the esophagus of an animal in an isolated state, or the corresponding esophageal region of a digestive tract model.

Step S3. The release source 10 injects air into the elastic clamp cavity 41 until the elastic clamp member 40 is expanded by the air pressure, so that the capsule endoscope 60 is released from the elastic clamp cavity 41.

Referring to the foregoing, when the endoscopic detection method is used, once the capsule endoscope 60 is inserted into the elastic clamp member 40, the elastic clamp member 40 can inflate and deform to apply a clamping force to the capsule endoscope 60, which is more reliable and prevents the capsule endoscope 60 from being detached from the elastic clamp member 40 due to insufficient force, thereby more reliably extending the time during which the capsule endoscope 60 stays in the target area.

The endoscopic method further comprises the following step before the step S1.

Step S0: The tether 20 is winded around the capsule endoscope 60 from the end connected to the elastic clamp member 40 to form the spiral structure 21. The spiral structure 21 can be gradually unwound with the movement of the capsule endoscope 60 in a clamped state. The inner side of the spiral structure 21 forms a capsule accommodating cavity that is connected and placed in close proximity to the elastic clamp cavity 41.

With addition of the above step, the frequency and extent of pulling tether 20 can be reduced by the gradual unwinding of the spiral structure 21, which also provides buffering for the movement of the capsule endoscope 60, and finally a superior examination experience for the subject.

In the present application, "a release source" means a source that is configured to help to achieve a release stated or a release process. The release source can output air to generate an appropriate acting force.

The person skilled in the art realizes that the present invention by no means is limited to the preferred embodiments described above. On the contrary, many modifications and variations are possible within the scope of the appended claims. Any modifications, equivalent substitutions, improvements, etc. made within the spirit and principles of this disclosure are intended to be included within the scope of the present invention.

We claim:

1. An endoscope apparatus, comprising:
a release source, configured to generate an acting force;
a tether connected to the release source;
an elastic clamp member;
wherein the elastic clamp member comprises an elastic clamp cavity, and the elastic clamp cavity is interconnected to an air outlet of the release source through a tether;
a capsule endoscope;
wherein the capsule endoscope and the elastic clamp member are configured as:
in a clamped state, at least a portion of the capsule endoscope is within the elastic clamp cavity, the elastic clamp member has an ability to recover from deformation to apply a clamping force to the capsule endoscope;
in a released state, the elastic clamp member is expanded by an air pressure from the tether, and the capsule endoscope is released from the elastic clamp cavity,
wherein one end of the tether connected to the elastic clamp member set as a spiral structure, and the spiral structure forms a capsule accommodating cavity, the capsule accommodating cavity is connected and placed in close proximity to the elastic clamp cavity;
the spiral structure gradually unwinds with a movement of the capsule endoscope in the clamped state.

2. The endoscope apparatus of claim 1, wherein the spiral structure forms its shape using edible hydrosol.

3. The endoscope apparatus of claim 1, wherein a middle section of the capsule endoscope is a cylindrical section, the spiral structure is sleeved on the cylindrical section, and the spiral structure and the elastic clamp member are spaced apart.

4. The endoscope apparatus of claim 3, wherein an inner diameter of the spiral structure is greater than or equal to an outer diameter of the cylindrical section, and the difference between the inner diameter and the outer diameter is less than 1 mm.

5. The endoscope apparatus of claim 1, wherein a last turn of the spiral structure is closer to air inlet of the elastic clamp member than a first turn of the spiral structure.

6. The endoscope apparatus of claim 1, wherein the first turn of the spiral structure is closer to the air inlet of the elastic clamp member than the last turn of the spiral structure, and the portion of the tether from the last turn to the air inlet is located inside the spiral structure.

7. The endoscope apparatus of claim 6, wherein the portion of the tether connected to the first turn is a U-shaped-curvature structure, and the bent portion of the U-shaped-curvature structure is located inside the last turn of the tether.

8. The endoscope apparatus of claim 1, wherein the elastic clamp member comprises a spherical inner wall, and a maximum lateral diameter of the spherical inner wall is a first diameter and a maximum lateral diameter of the portion of the capsule endoscope in contact with the spherical inner wall is a second diameter; wherein the first diameter is smaller than the second diameter, the first diameter is 5 to 9 mm, and the second diameter is 9 to 20 mm.

9. The endoscope apparatus of claim 1, wherein the elastic clamping member and the capsule endoscope are set as:
in the clamped state, a ratio of a volume of the portion of the capsule endoscope in the elastic clamp cavity to a total volume of the capsule endoscope is between ⅕ and ½.

10. The endoscope apparatus of claim 1, further comprising a control system, wherein the capsule endoscope comprises a magnet unit, and the control system controls the orientation of the capsule endoscope by the magnet unit.

11. The endoscope apparatus of claim 1, wherein the tether is integrally formed with the elastic clamp member, and the tether and the elastic clamp member are made of different materials.

12. The endoscope apparatus of claim 1, wherein the tether comprises scale marks.

13. An endoscopic detection method for use in the endoscope apparatus according to claim 1, comprising the following steps:
step S1: at normal pressure, insert at least a portion of the capsule endoscope into the elastic clamp cavity, wherein the elastic clamp member has an ability to recover from deformation to apply a clamping force to the capsule endoscope;
step S2: place the capsule endoscope and the elastic clamp member into a target position under a traction of the tether;
step S3: inject air into the elastic clamp cavity by the release source until the elastic clamp member is expanded by the air pressure, so that the capsule endoscope is released from the elastic clamp cavity.

14. The endoscopic detection method of claim 13, before the step S1 further comprising:
wind the tether around the capsule endoscope from an end connected to the elastic clamp member to form a spiral structure that gradually unwinds with a movement of the capsule endoscope in a clamped state, wherein an inner side of the spiral structure forms a capsule accommodating cavity that is connected and placed in close proximity to the elastic clamp cavity.

* * * * *